(12) United States Patent
Kerrigan

(10) Patent No.: US 6,818,063 B1
(45) Date of Patent: Nov. 16, 2004

(54) STENT MANDREL FIXTURE AND METHOD FOR MINIMIZING COATING DEFECTS

(75) Inventor: Cameron Kerrigan, San Francisco, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 39 days.

(21) Appl. No.: 10/254,203

(22) Filed: Sep. 24, 2002

(51) Int. Cl.⁷ .............................................. B05C 13/02
(52) U.S. Cl. ........................ 118/500; 427/2.3; 427/2.28
(58) Field of Search ........................ 118/500, DIG. 11; 29/527.2; 427/2.3, 2.28; 623/1.46–1.48; 606/194; 269/48.1, 52

(56) References Cited

U.S. PATENT DOCUMENTS

| | | | |
|---|---|---|---|
| 4,733,665 A | 3/1988 | Palmaz | 128/343 |
| 4,800,882 A | 1/1989 | Gianturco | 128/343 |
| 4,886,062 A | 12/1989 | Wiktor | 127/343 |
| 5,037,427 A | 8/1991 | Harada et al. | 606/108 |
| 5,234,457 A | 8/1993 | Andersen | 606/198 |
| 5,537,729 A | 7/1996 | Kolobow | 29/527.2 |
| 5,628,786 A * | 5/1997 | Banas et al. | 623/1.13 |
| 5,772,864 A | 6/1998 | Møller et al. | 508/73 |
| 5,788,626 A | 8/1998 | Thompson | 600/36 |
| 5,895,407 A | 4/1999 | Jayaraman | 606/198 |
| 5,897,911 A | 4/1999 | Loeffler | 427/2.25 |
| 5,922,393 A | 7/1999 | Jayaraman | 427/2.3 |
| 5,935,135 A | 8/1999 | Bramfitt et al. | 606/108 |
| 6,010,573 A | 1/2000 | Bowlin | 118/620 |
| 6,056,993 A | 5/2000 | Leidner et al. | 427/2.25 |
| 6,120,847 A | 9/2000 | Yang et al. | 427/335 |
| 6,126,686 A * | 10/2000 | Badylak et al. | 623/1.24 |
| 6,153,252 A | 11/2000 | Hossainy et al. | 427/2.3 |
| 6,156,373 A | 12/2000 | Zhong et al. | 427/2.28 |
| 6,214,115 B1 | 4/2001 | Taylor et al. | 118/423 |
| 6,258,121 B1 | 7/2001 | Yang et al. | 623/1.46 |
| 6,322,847 B1 | 11/2001 | Zhong et al. | 427/2.28 |
| 6,364,903 B2 | 4/2002 | Tseng et al. | 623/1.15 |
| 6,387,118 B1 | 5/2002 | Hanson | 623/1.11 |
| 6,521,284 B1 * | 2/2003 | Parsons et al. | 427/2.24 |
| 6,527,863 B1 | 3/2003 | Pacetti et al. | 118/500 |

OTHER PUBLICATIONS

U.S. patent application Ser. No. 09/873,020 Villareal, filed May 31, 2001.
U.S. patent application Ser. No. 09/894,242, Moein, filed Jun. 27, 2001.
U.S. patent application Ser. No. 09/894,248, Pacetti et al., filed Jun. 27, 2001.
U.S. patent application Ser. No. 09/896,000, Pacetti et al., filed Jun. 28, 2001.
U.S. patent application Ser. No. 09/896,436, Pacetti et al., filed Jun. 28, 2001.
U.S. patent application Ser. No. 09/255,913, Tang et al., filed Sep. 26, 2002.

* cited by examiner

Primary Examiner—J. A. Lorengo
Assistant Examiner—Michelle Acevedo Lazor
(74) Attorney, Agent, or Firm—Cameron K. Kerrigan; Squire, Sanders & Dempsey

(57) ABSTRACT

A stent mandrel fixture for supporting a stent during the application of a coating substance is provided.

11 Claims, 3 Drawing Sheets

STENT MANDREL FIXTURE AND METHOD FOR MINIMIZING COATING DEFECTS

TECHNICAL FIELD

This invention relates to an apparatus used in the process of coating a stent, and more particularly provides a suction stent mandrel fixture and method for minimizing coating defects on stents.

BACKGROUND

Blood vessel occlusions are commonly treated by mechanically enhancing blood flow in the affected vessels, such as by employing a stent. Stents act as scaffolding, functioning to physically bold open and, if desired, to expand the wall of affected vessels. Typically stents are capable of being compressed, so that they can be inserted through small lumens via catheters, and then expanded to a larger diameter once they are at the desired location. Examples in the patent literature disclosing stents include U.S. Pat. No. 4,733,665 issued to Palmaz, U.S. Pat. No. 4,800,882 issued to Gianturco, and U.S. Pat. No. 4,886,062 issued to Wiktor.

FIG. 1 illustrates a conventional stent 10 formed from a plurality of struts 12. The plurality of struts 12 are radially expandable and interconnected by connecting elements 14 that are disposed between adjacent struts 12, leaving lateral openings or gaps 16 between adjacent struts 12. Struts 12 and connecting elements 14 define a tubular stent body having an outer, tissue-contacting surface and an inner surface.

Stents are used not only for mechanical intervention but also as vehicles for providing biological therapy. Biological therapy can be achieved by medicating the stents. Medicated stents provide for the local administration of a therapeutic substance at the diseased site. Local delivery of a therapeutic substance is a preferred method of treatment because the substance is concentrated at a specific site and thus smaller total levels of medication can be administered in comparison to systemic dosages that often produce adverse or even toxic side effects for the patient.

One method of medicating a stent involves the use of a polymeric carrier coated onto the surface of the stent. A composition including a solvent, a polymer dissolved in the solvent, and a therapeutic substance dispersed in the blend is applied to the stent by immersing the stent in the composition or by spraying the composition onto the stent. The solvent is allowed to evaporate, leaving on the stent surfaces a coating of the polymer and the therapeutic substance impregnated in the polymer.

A shortcoming of the above-described method of medicating a stent is the potential for coating defects. While some coating defects can be minimized by adjusting the coating parameters, other defects occur due to the nature of the interface between the stent and the apparatus on which the stent is supported during the coating process. A high degree of surface contact between the stent and the supporting apparatus can provide regions in which the liquid composition can flow, wick, and collect as the composition is applied. As the solvent evaporates, the excess composition hardens to form excess coating at and around the contact points between the stent and the supporting apparatus. Upon the removal of the coated stent from the supporting apparatus, the excess coating may stick to the apparatus, thereby removing some of the coating from the stent and leaving bare areas. Alternatively, the excess coating may stick to the stent, thereby leaving excess coating as clumps or pools on the struts or webbing between the struts.

Accordingly, a new stent mandrel fixture is needed to minimize coating defects.

SUMMARY

In accordance with one embodiment, an apparatus for supporting a stent during the process of applying a coating substance to the stent is provided, comprising a mandrel having a hollow tubular body and pores disposed on the surface of the mandrel, the pores extending through the body; and a vacuum device in fluid communication with the mandrel for extracting the coating substance that is applied to the stent. The apparatus can also include a coupling for allowing the mandrel to rotate with respect to the vacuum device. In one embodiment, the apparatus additionally includes a first member connected to one end of the mandrel and a second member connected to the other end of the mandrel, wherein the mandrel is disposed through a longitudinal bore of the stent. The stent can be supported by the first and second members of the apparatus such that the mandrel does not contact an inner surface of the stent. The first member can be moved incrementally closer to the second member for securing the stent between the first and second members.

In accordance with another embodiment, an apparatus is provided, comprising a first member for supporting a first end of a stent; a second member for supporting a second end of the stent; a third member connecting the first member to the second member and extending through a longitudinal bore of the stent, the third member having a longitudinal bore, and the third member having pores on a surface of the third member, the pores extending all the way through the surface to the bore; and a vacuum device in fluid communication with the bore of the third member for applying a vacuum pressure so as to extract any excess coating substance that is applied to the stent during a process of coating the stent. In one embodiment, the first and second members are generally coned shaped and capable of penetrating at least partially into the ends of the stent. As a result, when a stent is positioned on the apparatus, the exterior surface of the third member does not contact the inner surface of the stent during the application of the coating substance. The coned shaped first and second members can be hollow and in fluid communication with the bore of the third member. The coned shaped ends can include pores disposed on the surface thereof for allowing the vacuum device to extract the coating substance that is deposited on the first and second members.

In accordance with another embodiment of the invention, a stent coating device is provided, comprising: a mandrel for being inserted at least partially through a longitudinal bore of a stent, the mandrel having a hollow tubular body and pores formed on the surface of the mandrel, the pores extending all the way through the body; and a vacuum device in fluid communication with the mandrel for collecting excess coating composition that is applied to the stent.

In accordance with another embodiment, a method of coating a stent is provided, comprising: inserting a stent over a mandrel having a hollow tubular body and pores disposed on the surface of the mandrel, the pores extending through the body; applying a coating composition to the stent; and applying a vacuumed pressure to the hollow tubular body for extracting the coating composition that is applied to the stent. The coating composition can be applied by spraying the composition onto the stent. In one embodiment, the stent can be rotated about the longitudinal axis of the stent. The coating composition can include a polymer dissolved in a solvent and a therapeutic substance optionally added thereto. The outer surface of the mandrel can contact the inner surface of the stent. Alternatively, the outer surface of the mandrel does not contact the inner surface of the stent.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

DETAILED DESCRIPTION

Figure 1:
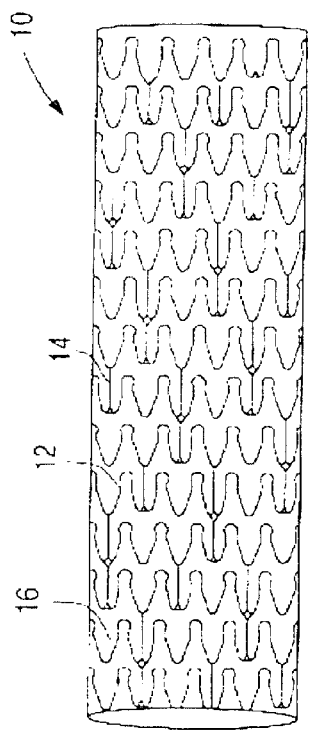
FIG. 1 illustrates a conventional stent.
Figure 2:
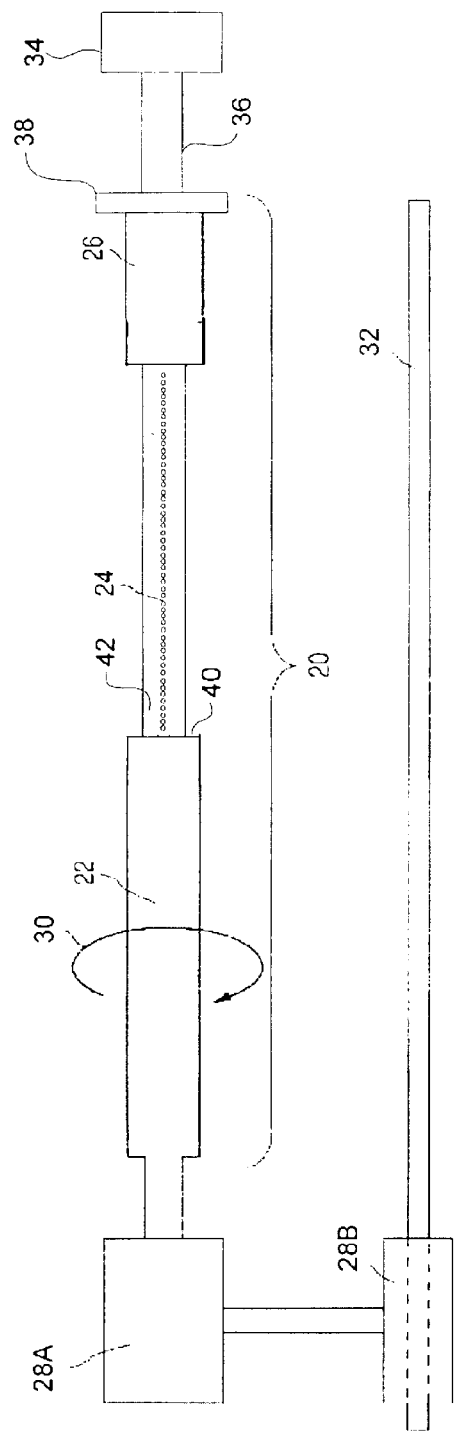
FIG. 2 illustrates a stent mandrel fixture in accordance with an embodiment of the invention.
Figure 3:
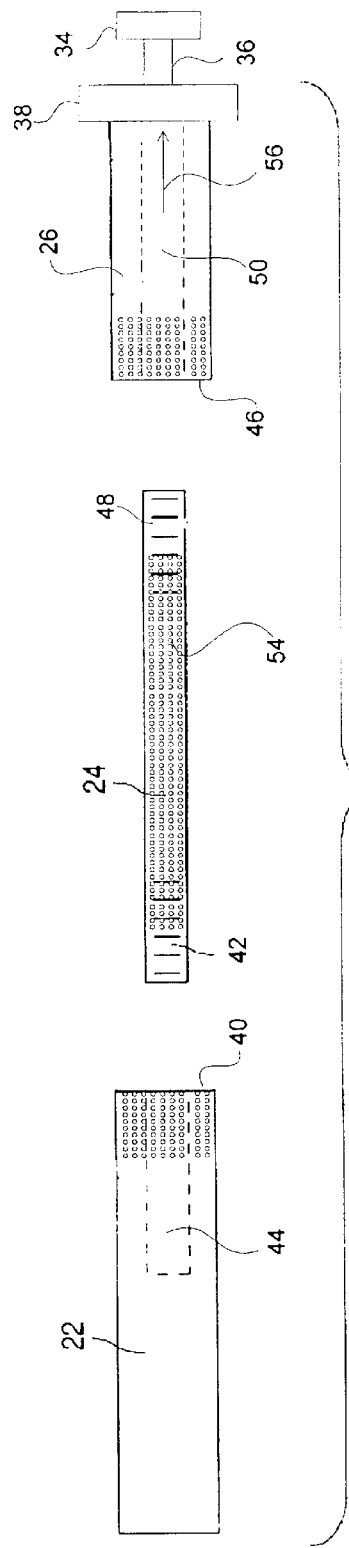
FIG. 3 illustrates an expanded view of stent mandrel fixture of FIG. 2.

FIGS. 2 and 3 illustrate a stent mandrel fixture 20 in accordance with an embodiment of the invention. Fixture 20 for supporting a stent includes a support member 22, a mandrel 24, and a lock member 26. Support member 22 can connect to a motor 28A so as to provide rotational motion about the longitudinal axis of a stent, as depicted by arrow 30, during the coating process. Another motor 28B can also be provided for moving fixture 20 in a linear direction, back and forth, along a rail 32. The type of stent that can be crimped on mandrel 24 is not of critical significance. The term stent is broadly intended to include self- and balloon-type expandable stents as well stent-grafts.

Stent mandrel fixture 20 is in fluid communication with a vacuum device 34 for collecting excess composition that is applied to the stent. Lock member 26 is coupled to vacuum device 34 via a conduit 36. A coupler 38 allows mandrel fixture 20 to rotate with respect to conduit 36 and vacuum device 34.

Support member 22 includes a flat end 40 that is coupled to a first end 42 of mandrel 24. In accordance to one embodiment, mandrel 24 can be permanently affixed to support member 22. Alternatively, support member 22 can include a bore 44 for receiving first end 42 of mandrel 24. First end 42 of mandrel 24 can be threaded to screw into bore 44. Alternatively, a non-threaded first end 42 of mandrel 24 can be press-fitted or friction-fitted within bore 44. Bore 44 should be deep enough so as to allow mandrel 24 to securely mate with support member 22. The depth of bore 44 can be over-extended so as to allow a significant length of mandrel 24 to penetrate bore 44. This would allow the length of mandrel 24 to be adjusted to accommodate stents of various sizes.

Lock member 26 includes a flat end 46 that can be permanently affixed to a second end 48 of mandrel 24 if end 42 of mandrel 24 is disengagable from support member 22. A bore 50 extends along lock member 26 for allowing mandrel 24 to be in fluid communication with vacuum device 34. In accordance with another embodiment, mandrel 24 can have a threaded second end 48 for screwing into bore 50. A non-threaded second end 48 and bore 50 combination can also be employed such that second end 48 of mandrel 24 is press-fitted or friction-fitted within bore 50. Lock member 26 can be incrementally moved closer to support member 22. Accordingly, stents of any length can be securely pinched between flat ends 40 and 46 of the support and lock members 22 and 26. A stent need not, however, be pinched between ends 40 and 46. A stent can be simply crimped tightly on mandrel 24.

Figure 4:
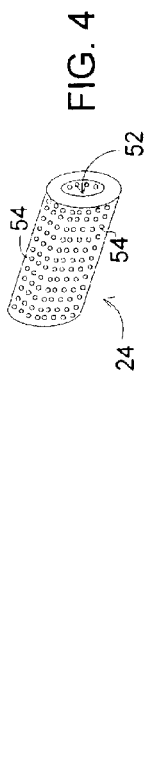
FIG. 4 illustrates a perspective view of a part of the stent mandrel fixture of FIG. 2.

Mandrel 24, as illustrated by FIG. 4, includes a hollow tubular body having a bore 52 extending through the body of mandrel 24. Mandrel 24 has pores 54 on its surface that are in communication with bore 52. In other words, pores 54 penetrate all the way through the body of mandrel 24. Bore 52 and pores 54 can be of any suitable size and any number of pores 54 can be provided for effectively allowing the coating composition to be vacuumed off of the stent and mandrel 24. Pore size and number depend of a variety of factors including the viscosity of the composition used, if the composition is in a saturated state or if it includes particles, and the power of vacuum that is applied to mandrel 24. In accordance to one embodiment, ends 40 and 46 may also include pores 54 for extraction of any excess coating composition.

Figure 5:
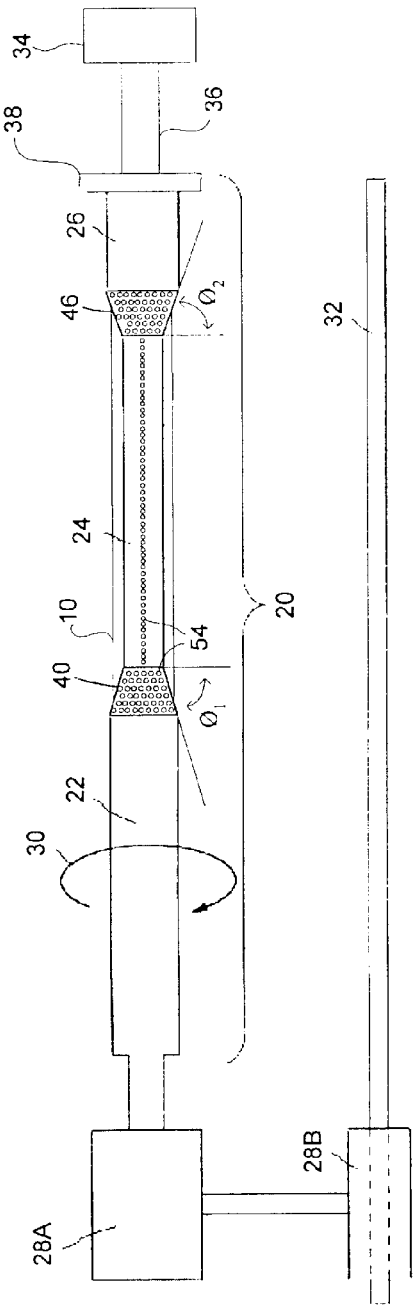
FIG. 5 illustrates a stent mandrel fixture according to another embodiment of the invention.

FIG. 5 illustrates a view of stent mandrel fixture 20 according to another embodiment of the invention. Support member 22 and lock member 26 include coning end portions 40 and 46, instead of flat ends, for penetrating into ends of stent 10. The coning end portions 40 and 46 can taper inwardly at an angle $\emptyset_1$ of about 15° to about 75°, more narrowly from about 30° to about 60°. By way of example, angle $\emptyset_1$ can be about 45°. The outer diameter of mandrel 24 can be smaller than the inner diameter of stent 10, as positioned on fixture 20, so as to prevent the outer surface of mandrel 24 from making contact with the inner surface of stent 10. As best illustrated by FIG. 5, a sufficient clearance between the outer surface of mandrel 24 and the inner surface of stent 10 is provided to prevent mandrel 24 from obstructing the pattern of the stent body during the coating process. By way of example, the outer diameter of mandrel 24 can be from about 0.010 inches (0.254 mm) to about 0.017 inches (0.432 mm) when stent 10 has a mounted inner diameter of between about 0.025 inches (0.635 mm) and about 0.035 inches (0.889 mm). In this embodiment, contact between stent 10 and fixture 20 is limited as stent 10 only rests on coning ends 40 and 46. Coning ends 40 and 46 as well as mandrel 24 can include pores 54 for allowing excess coating composition to be extracted by vacuum device 34.

In order to minimize coating defects from forming on stent 10 during the coating process, vacuum device 34 applies a suction force to bore 50 of lock member 26 and bore 52 of mandrel 24. The suction force should be of a force strong enough to extract the excess coating material. For example, the suction force could be greater than a 0.1 atmosphere pressure difference between the interior of mandrel 24 (i.e., bore 52) and exterior to mandrel 24. The suction force then pulls excess coating into vacuum device 34, as indicated by arrow 56, for storage, disposal, or recycling and reapplication of the coating substance.

Figure 6:
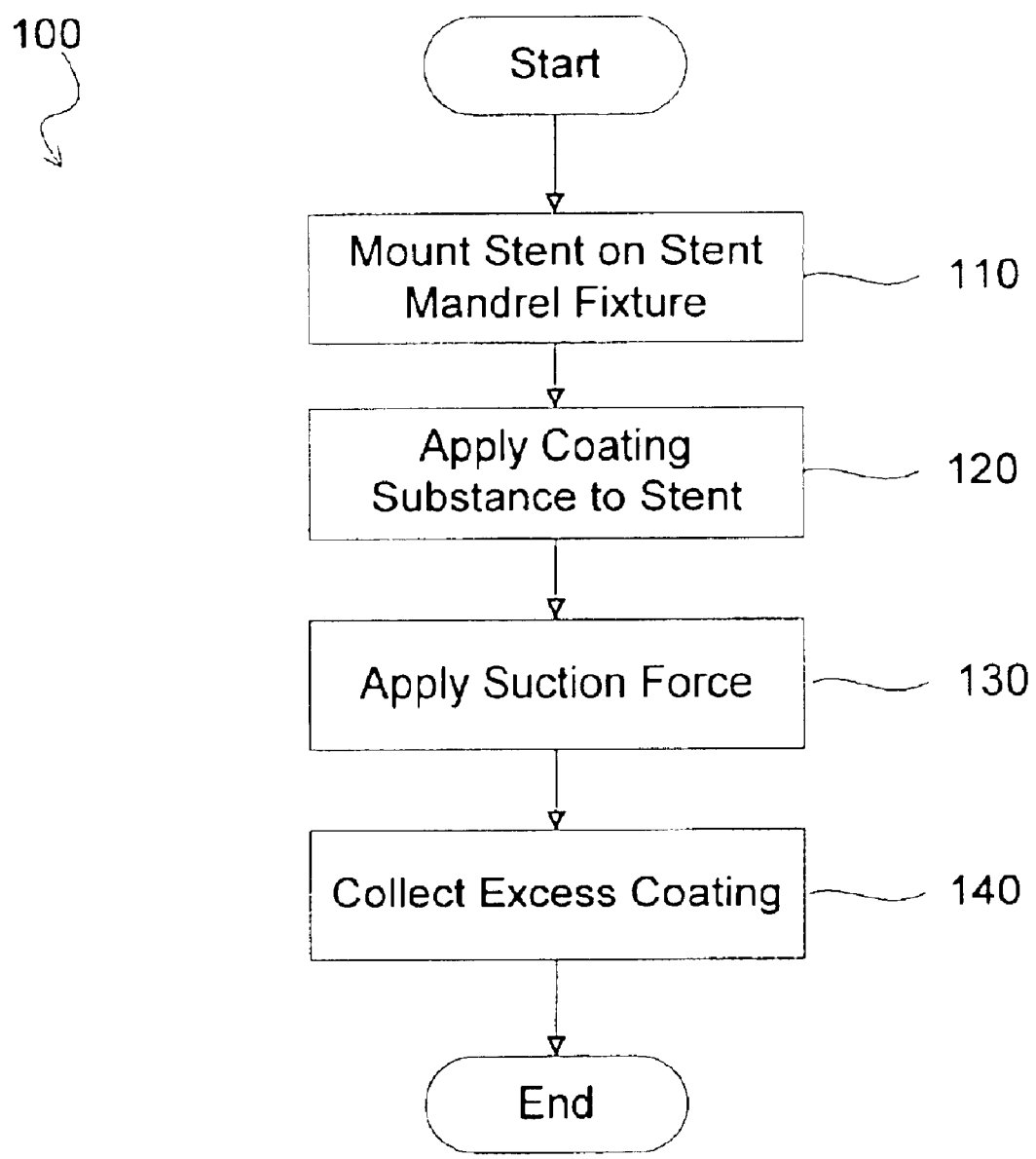
FIG. 6 illustrates a flowchart of a method for minimizing coating defects using the stent mandrel fixture.

FIG. 6 illustrates a flowchart of a method 100 for minimizing coating defects using suction mandrel fixture 20. First, a stent, such as stent 10, is mounted (110) on stent mandrel fixture 20. For fixture 20 illustrated in FIG. 2, the stent can be crimped directly onto mandrel 24. For fixture 20 of FIG. 5, the stent is securely pinched between ends 40 and 46 so that the stent does not make contact with mandrel 24. Next, a coating substance is applied (120), for example by spraying, to the stent. The stent can be rotated about the longitudinal axis of the stent and/or moved in a linear direction, back and forth, passed the spray nozzle. During the application (120) of the coating substance and/or after the application (120) of coating substance, suction force is applied (130). After suction is applied (130), the excess coating sucked into the interior of mandrel fixture 20 is collected (140) in vacuum device 34. The excess coating can then be recycled and reapplied, stored, or disposed of in an appropriate manner.

The coating substance can include a solvent and a polymer dissolved in the solvent and optionally a therapeutic substance or a drug added thereto. Representative examples of polymers that can be used to coat a stent include ethylene vinyl alcohol copolymer (commonly known by the generic name EVOH or by the trade name EVAL); poly(hydroxyvalerate); poly(L-lactic acid); polycaprolactone; poly(lactide-co-glycolide); poly(hydroxybutyrate); poly(hydroxybutyrate-co-valerate); polydioxanone; polyorthoester; polyanhydride; poly(glycolic acid); poly(D,L-lactic acid); poly(glycolic acid-co-trimethylene carbonate); polyphosphoester; polyphosphoester urethane; poly(amino acids); cyanoacrylates; poly(trimethylene carbonate); poly(iminocarbonate); copoly(ether esters) (e.g., PEO/PLA); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrilestyrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; and carboxymethyl cellulose.

"Solvent" is defined as a liquid substance or composition that is compatible with the polymer and is capable of dissolving the polymer at the concentration desired in the composition. Examples of solvents include, but are not limited to, dimethylsulfoxide, chloroform, acetone, water (buffered saline), xylene, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, isopropanol admixed with water, N-methyl pyrrolidinone, toluene, and mixtures and combinations thereof.

The therapeutic substance or drug can be for inhibiting the activity of vascular smooth muscle cells. More specifically, the active agent can be aimed at inhibiting abnormal or inappropriate migration and/or proliferation of smooth muscle cells for the inhibition of restenosis. The active agent can also include any substance capable of exerting a therapeutic or prophylactic effect in the practice of the present invention. For example, the agent can be for enhancing wound healing in a vascular site or improving the structural and elastic properties of the vascular site. Examples of agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, antiinflammatory, antiplatelet, anticoagulant, antifibrin, antithrombin, antimitotic, antibiotic, antiallergic and antioxidant substances. Examples of such antineoplastics and/or antimitotics include paclitaxel (e.g., TAXOL® by Bristol-Myers Squibb Co., Stamford, Conn.), docetaxel (e.g., Taxotere®, from Aventis S. A., Frankfurt, Germany), methotrexate, azathioprine, vincristine, vinblastine, fluorouracil, doxorubicin hydrochloride (e.g., Adriamycin® from Pharmacia & Upjohn, Peapack N.J.), and mitomycin (e.g., Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.). Examples of such cytostatic or antiproliferative agents include angiopeptin, angiotensin converting enzyme inhibitors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, dexamethasone, and rapamycin.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. An apparatus for supporting a stent during the process of applying a coating substance to the stent, comprising:

a mandrel having a hollow tubular body and pores disposed on the surface of the mandrel, the pores extending through the body and configured to receive a coating substance;

a vacuum device in fluid communication with the mandrel for extracting the coating substance that is applied to the stent; and a coupling for allowing the mandrel to rotate with respect to the vacuum device.

2. The apparatus of claim 1, wherein the apparatus additionally includes a first member connected to one end of the mandrel and a second member connected to the other end of the mandrel, wherein the mandrel is disposed through a longitudinal bore of the stent, wherein the first member can be moved incrementally closer to the second member for securing the stent between the first and second members.

3. The apparatus of claim 2, wherein the stent is supported by the first and second members of the apparatus such that the mandrel does not contact an inner surface of the stent.

4. An apparatus, comprising:

a first member to support a first end of a stent;

a second member to support a second end of the stent;

a third member connecting the first member to the second member and extending through a longitudinal bore of the stent, the third member having a longitudinal bore, and the third member having pores on a surface of the third member, the pores extending all the way through the surface to the bore; and a vacuum device in fluid communication with the bore of the third member to apply a vacuum pressure so as to extract any excess coating substance that is applied to the stent during a process of coating the stent.

5. The apparatus of claim 4, wherein the vacuum device is coupled via a coupler to the second member, the coupler allowing the first, second and third members to rotate with respect to the vacuum device.

6. The apparatus of claim 4, wherein the second member includes a bore for allowing the bore of the third member to be in fluid communication with the vacuum device.

7. The apparatus of claim 4, wherein the first and second members are generally coned shaped and capable of penetrating at least partially into the ends of the stent.

8. The apparatus of claim 7, wherein coned shaped first and second members are hollow and in fluid communication with the bore of the third member, the coned shaped ends include pores disposed on the surface thereof for allowing the vacuum device to extract the coating substance that is deposited on the first and second members.

9. The apparatus of claim 4, wherein when a stent is positioned on the apparatus, the exterior surface of the third member does not contact the inner surface of the stent during the application of the coating substance.

10. A stent coating device, comprising:

a mandrel for being inserted at least partially through a longitudinal bore of a stent, the mandrel having a hollow tubular body and pores formed on the surface of the mandrel, the pores extending all the way through the body and configured to receive a coating composition;

a vacuum device in fluid communication with the mandrel for collecting excess coating composition that is applied to the stent; and a means for rotating the mandrel about a longitudinal axis of the stent.

11. A stent coating device, comprising:

a mandrel for being inserted at least partially through a longitudinal bore of a stent, the mandrel having a hollow tubular body and pores formed on the surface of the mandrel, the pores extending all the way through the body and configured to receive a coating composition;

a vacuum device in fluid communication with the mandrel for collecting excess coating composition that is applied to the stent;

a means for rotating the mandrel about a longitudinal axis of the stent; and a means for allowing the mandrel to rotate with respect to the vacuum device.

* * * * *